United States Patent [19]

Balingit et al.

[11] 4,243,659

[45] Jan. 6, 1981

[54] COMPOSITIONS FOR IMPROVING HAIR BODY AND METHOD OF USE

[75] Inventors: Angelina T. Balingit, Chicago; Anthony A. Scafidi, Bellwood, both of Ill.

[73] Assignee: Alberto-Culver Company, Melrose Park, Ill.

[21] Appl. No.: 41,945

[22] Filed: May 24, 1979

[51] Int. Cl.³ .......................... A61K 7/06; A61K 7/11
[52] U.S. Cl. ..................................... 424/70; 252/89.1; 424/71; 424/72
[58] Field of Search ............................. 424/70, 71, 72

[56] References Cited

U.S. PATENT DOCUMENTS

| | | | |
|---|---|---|---|
| 2,437,965 | 3/1948 | Michaels et al. | 424/71 |
| 2,817,342 | 12/1957 | Henkin | 424/71 X |
| 2,836,185 | 5/1958 | Hervey | 424/71 X |
| 2,847,351 | 8/1958 | Brown et al. | 424/71 |
| 2,983,569 | 5/1961 | Charle et al. | 424/71 |

FOREIGN PATENT DOCUMENTS

| | | | |
|---|---|---|---|
| 649282 | 12/1964 | Belgium | 424/72 |
| 1904159 | 8/1969 | Fed. Rep. of Germany | 424/319 |
| 2131404 | 12/1972 | Fed. Rep. of Germany | 424/319 |
| 2524297 | 12/1975 | Fed. Rep. of Germany | 424/319 |
| 1586682 | 11/1970 | France | 424/319 |
| 1129527 | 10/1968 | United Kingdom | 424/72 |

*Primary Examiner*—Dale R. Ore
*Attorney, Agent, or Firm*—Tilton, Fallon, Lungmus & Chestnut

[57] ABSTRACT

A liquid composition for increasing hair body by permanently swelling hair shafts with reduced loss of tensile strength comprises an aqueous solution of a hair cleansing synthetic detergent containing a bisulfite salt and dimethyl urea. The composition also preferably contains a cationic hair conditioner and hydroxyalkyl solvent. An amphoteric detergent base is preferred. The composition may be applied and rinsed out with water after a few minutes to increase hair body, and the applications may be repeated to further swell the hair without undue damage to the hair.

20 Claims, No Drawings

COMPOSITIONS FOR IMPROVING HAIR BODY AND METHOD OF USE

BACKGROUND AND PRIOR ART

Women with fine, hard-to-manage hair experience a need to build more body and thickness into their hair. Hair waving lotions can be used for this purpose, such as those containing a salt of thioglycolic acid. The hair is treated with the waving lotion and set on large rollers. After several minutes of reaction, it is rinsed with water and treated with a solution of hydrogen peroxide. This treatment swells the hair shafts, thereby increasing the body of the hair and giving the appearance of a fuller head of hair. A disadvantage of this procedure is that the hair shafts are damaged, tensile break strength being appreciably reduced, especially if the treatment is repeated. Since it may be desirable to treat fine hair to increase its body at frequent intervals, such as every one to two weeks, the use of waving lotions for this purpose can result in serious damage to the hair.

Hair waving lotions containing bisulfite salts, such as sodium bisulfite, are known, although they have not been widely used on a commercial basis. See, for example, U.S. Pat. Nos. 2,836,185, 2,836,543, 2,817,342, and 3,583,408. These patents also propose the use of nitrogen compounds, such as amines and amides, in combination with the bisulfite salt to promote swelling of the hair. Under certain conditions of use it is disclosed that a sulfite-amide composition can result in reduced hair damage (U.S. Pat. Nos. 2,836,185 and 2,836,543), but U.S. Pat. No. 3,583,408 proposes the use of a polymerizable vinylic monomer as an auxiliary treating agent to compensate for the loss of strength of the hair due to treatments with reagents such as bisulfite and urea. U.S. Pat. No. 2,836,543 proposes the use of auxiliary swelling agents such as pyrocatechol or gentisic acid.

SUMMARY OF INVENTION

In accordance with the present invention, the liquid base of the composition for increasing hair body comprises an aqueous solution of a hair cleansing synthetic detergent in an effective hair washing concentration for undiluted application. There is incorporated in this base solution an effective concentration of a bisulfite salt to reduce the cystine (—S—S—) linkages of the hair, thereby permitting swelling of the hair shafts to occur. The composition also contains a limited concentration of a specific swelling agent (N.N'-dimethyl urea), such as preferably 3 to 8% by weight. The pH is preferably controlled to minimize bleaching of the hair and to substantially prevent alkaline hydrolysis. In preferred embodiments, the composition also contains a small amount of cationic hair conditioner, which can be incorporated without difficulty where the synthetic detergent is an amphoteric detergent fully compatible with cationic nitrogen compounds. Also, an auxiliary swelling agent may be included, such as a minor proportion of a water-miscible hydroxyalkyl solvent.

Compositions of the kind described can be used for increasing hair body by permanently swelling hair shafts with reduced loss of tensile strength. By having the bodying agents in the detergent solution, the treatment of the hair can be carefully controlled. The composition is applied full strength, lathered as a shampoo, and left on the hair with the reducing and swelling agents acting in the presence of the detergent. To terminate the treatment all that is required is to quickly rinse the hair in water, the presence of the detergent assuring that the reducing and swelling agents will be immediately and thoroughly removed. The cationic conditioning agents, being substantive to the hair, will remain thereon, and it is believed that their action will help to offset any damage to the hair. It is believed that the thoroughness of removal of the reducing and swelling agents because of the presence of the detergent encourages the immediate re-forming of at least a portion of the cystine cross-links that were broken by the reducing action. Also, after the hair is dry, air oxidation will promote further re-forming of the cystine bonds.

DETAILED DESCRIPTION

In practicing the present invention, it is important to employ as the base of the liquid composition an aqueous solution of a hair cleansing synthetic detergent in an effective hair washing concentration for undiluted application. For example, the concentration on the basis of the total liquid composition can range from 5 to 20% by weight, such as a concentration of about 10%. Any synthetic hair cleansing detergent can be used which is compatible with the other ingredients, including nonionic, cationic and anionic synthetic detergents. However, it is preferred to employ an amphoteric detergent, such as cocoamidopropyl betaine or cocobetaine. Such amphoteric detergents are available commercially. (Richardson Company, Lemont, Ill.) Imidazoline detergents can also be used, such as Miranol C2M (Miranol Chemical Co., Irvington, N.J.)

The bisulfite salt may be selected from sodium, potassium, or ammonium bisulfite, or mixtures of such bisulfite salts. Sodium bisulfite is a convenient and desirable reagent. Based on the total composition, the bisulfite salt may be used within the range from 2 to 12% by weight, such as a concentration of about 8.0%. The bisulfite salt should be fully dissolved, and therefore should not be employed at or above its solubility limit.

In accordance with the present invention, the principal swelling agent for use in combination with the bisulfite-containing detergent solution is N.N'-dimethyl urea. No equivalent for this specific compound has been found. Further, the amount of the dimethyl urea should be limited. More specifically, the concentration based on the total liquid composition should be within the range from 2 to 12% by weight, such as a concentration of about 5 to 5.5%.

As an auxiliary swelling agent, there may be optionally incorporated a minor proportion of a hydroxyalkyl solvent. For example, hydroxyalkyl liquid compounds such as propylene glycol, glycerine, or hexylene glycol can be used. Alternatively, or additionally, lower monohydric alcohols can be used, such as ethanol or isopropanol. More generally, the preferred class of auxiliary swelling agents comprises water-miscible hydroxyalkyl solvents containing from 1 to 3 hydroxyl groups and from 2 to 6 carbons. The amount of the hydroxyalkyl solvent can range from 2 to 25% by weight based on the total composition, such as about 5%.

As indicated, it is also desirable to incorporate one or more cationic hair conditioners. Such agents are well known in the cosmetic art. For example, a compound such as isostearyl amido propyl morpholine lactate may be used. This is available as Richamate ISML from Richardson Co. Other fatty quaternary conditioning agents can be used, or cationic polymers having conditioning action, such as the water-soluble cationic cellulose resins. Such conditioning agents are available commercially as Polymers JR (Union Carbide Corp., New York, N.Y.). Further, a combination of such cationic conditioning agents can be used. All of these agents have the property of being substantive to the keratin of hair. Where the cationic conditioning agent employed is not compatible with an anionic detergent, the detergent base should be selected to avoid anionic-cationic reaction. Only a small amount of the cationic conditioning agents need be incorporated, such as from 0.5 to 3.0% based on the weight of the total composition. Typically, a combination of cationic conditioning agents in a combined amount of about 1 to 2% will be advantageous.

Other ingredients may also be included in the composition for commercial purposes, such as a preservative, perfume, etc. Any of the standard preservatives can be used, such as methyl or propyl paraben, formaldehyde, and the like. Usually, these minor ingredients will comprise less than one percent by weight of the composition.

A preferred formula is set out below. It will be understood that water is added to provide the balance of the parts by weight. In general, the amount of water present may range from about 60 to 80% by weight.

| Preferred Formula | |
|---|---|
| Principal Ingredients | weight % |
| Bisulfite salt | 6.5–8.5 |
| N.N'-dimethyl urea | 3–8 |
| Amphoteric detergent | 6–15 |
| Hydroxyalkyl solvent | 3–10 |
| Cationic hair conditioner | 0.5–3.0 |
| Water | q.s. |

The pH of compositions prepared in accordance with this invention should be adjusted so that they are mildly acid, for example, a pH in the range from 4.0 to 6.9. Preferably, however, the pH is adjusted to a pH within the range from 6.0 to 6.6, thereby minimizing bleaching of the hair as well as alkaline hydrolysis of the hair. Any standard base can be used for adjusting the pH, such as sodium or potassium hydroxide. Where the bisulfite is added as sodium bisulfite, it is believed that the most desirable base is ammonium hydroxide, thereby providing both ammonium and sodium ions in common with the bisulfite ions.

The present invention and the results which can be obtained therewith are further illustrated by the following examples.

EXAMPLE I

This example is intended to illustrate the best mode of practicing this invention as presently known. A liquid composition for increasing hair body is prepared in accordance with the following formula.

| Specific Formula (pH 6.0–6.4)[1] | |
|---|---|
| Ingredients | Weight % |
| Sodium bisulfite | 7.88 |
| N . N'-dimethyl urea | 5.20 |
| Cocoamidopropyl betaine[2] (30% in H$_2$O) | 30.00 |
| Propylene glycol | 5.00 |
| Cationic conditioners[3] (active basis) | 1.60 |
| Preservative[4] | 0.20 |

| -continued Specific Formula (pH 6.0–6.4)[1] | |
|---|---|
| Ingredients | Weight % |
| Perfume | 0.60 |
| Water[5] | q.s. |

[1] Adjusted by adding 28% NH$_4$OH.
[2] Chemadene Na 30, Richardson Co., Lemont, Illinois
[3] 0.60% Polymer JR 30M (Cationic cellulose resin) Union Carbide Corp., New York, N. Y.; and 4.00% Richamate ISML (isostearyl amido propyl morpholine lactate, 25% in H$_2$O), Richardson Co., Lemont, Illinois
[4] 37% formaldehyde
[5] Added to bring total formula to 100% (approx. 46.6%)

For the purpose of increasing hair body, the foregoing composition can be advantageously employed as follows:

(1) Shampoo about 0.5 ounces of the composition into wet hair, and rinse the hair with water.

(2) Apply about 0.5 ounces of the composition, and leave on the hair at room temperature for about 15 minutes.

(3) Rinse the hair thoroughly with water to remove residue of composition, and then dry the hair and style as desired.

The foregoing procedure is preferred for the first treatment of the hair. For subsequent treatments, the same procedure can be used, except that in step 2 the composition is left on the hair for five minutes.

More generally, the composition may be applied to the hair in a sufficient amount to coat the hair and left thereon for from 3 to 20 minutes, and then rinsed out of the hair with water. This treatment can be repeated at intervals of from 5 to 20 days, that is, the treatments are preferably spaced apart by at least five days. Preferably, the composition when applied is massaged into wet hair, thereby promoting the distribution of the composition over the hair.

EXAMPLE II

Using the composition of Example I, the swelling effect on hair fibers was studied. The data obtained is summarized below in Table A. The procedure used was as follows:

Cut the hair fibers 3 in. long. Glue 3 fibers parallel to each other and about 2 mm. apart on the slide. Mount the fibers securely with tape at both ends of the slide leaving about 2 mm. open at the center for measuring the diameter of each strand. Using a Bausch & Lomb Laboratory Microscope with standard 10X eyepiece and an eyepiece scale, before treatment, focus the fiber under the microscope with 43X objective, 0.65 N.A. Record the reading on the eyepiece scale. Then treat the fibers as follows: (1) Apply a drop of the test composition on the fibers and cover with a cover glass. Set the slide on a hot plate @ 37° C. for 15 minutes. Using a wash bottle, rinse thoroughly with deionized water. Dry the fibers for 5 minutes with the aid of an electric blow-dryer. Again, measure the diameter under the microscope. (2) For subsequent treatments, repeat the same procedure, but leave the test composition on hair for only 5 minutes instead of 15 minutes. The % swelling is calculated as:

% Swelling = (B-A)/A × 100 where A equals the diameter of hair before treatment, and B equals the diameter of hair after treatment.

TABLE A

PERMANENT HAIR SWELLING OBTAINED WITH EXAMPLE I COMPOSITION

| Number of Treatments | 0 | 1 | 2 | 3 | 4 | 5 | 6 |
| --- | --- | --- | --- | --- | --- | --- | --- |
|  | 56.33 | 61.33 | 66.33 | 68.00 | 75.33 | 76.33 | 77.0 |
|  | 51.66 | 54.00 | 56.00 | 56.66 | 57.33 | 58.33 | 59.0 |
|  | 52.00 | 54.00 | 58.00 | 58.66 | 59.33 | 60.66 | 63.0 |
| Diameter of Hair | 50.66 | 52.66 | 53.66 | 56.00 | 57.00 | 58.00 | 58.66 |
|  | 23.66 | 24.33 | 25.33 | 25.66 | 26.50 | 27.16 | 27.16 |
|  | 35.66 | 37.00 | 38.00 | 39.00 | 39.66 | 40.16 | 40.16 |
|  | 52.66 | 55.00 | 56.66 | 58.33 | 59.33 | 59.33 | 59.33 |
| Average | 46.09 | 48.33 | 50.57 | 51.76 | 53.50 | 54.28 | 54.90 |
| % Swelling |  | 4.86% | 9.72% | 12.30% | 16.08% | 17.77% | 19.11% |

EXAMPLE III

The loss of hair tensile strength with repeated treatments using the composition of Example I was studied, using an Instron Break-Strength Instrument (Instron Engineering Corp., Canton, Mass.). For comparison, a commercial waving lotion was included in the test, the lotion containing ammonium thioglycollate as the principal active ingredient. The data obtained is summarized below in Table B. Table C represents values computed from the data of Table B, the numerical values for break strength as shown in Table B being converted to percent loss of break strength. The procedure used was:

Preparation of Samples

Cut the hair fibers 4 in. long. Weigh 20 fibers individually and record each weight. Tape one end of each fiber and label it 1–20. Place the hair in a Pyrex petri dish and treat the hair as follows: (1) Apply 1 gm. of the test composition on the hair and place it on a hot plate @ 37° C. for 15 minutes. Then rinse the hair thoroughly with tap water. Air-dry at room temperature. Determine break-strength by the Instron Test Instrument. (2) For subsequent treatments repeat the same procedure on another set of 20 fibers, but leave the test composition on hair for only 5 minutes instead of 15 minutes. Weigh another set of 20 fibers to serve as the control (untreated), and determine break-strength likewise by the Instron Test Instrument.

Break Strength Determination

The prepared fibers of 4.0 inch lengths are weighed to the nearest 0.01 mg. They are then tabbed with white tape and numbered. 1.5 inches of each end of the fiber is then mounted between two layers of transparent tape and equilibrated in a constant humidity environment set at 50% R.H. overnight. The fibers are mounted on the Instron so that the center 1.0 inch of the fiber remains exposed between the jams (clamps) of the instrument. The fibers are then pulled to break under the following conditions:

| Gage Length: | 1.0 inch |
| --- | --- |
| Cross Head Speed: | 2 inch/min. |
| Cell: | B |
| Chart Speed: | 10 inch/min. |
| Load: | 200 grams |

Calculations

The weight of the fiber is used to calculate the volume of the fiber V = Wt. (mgs)/fiber density assuming a constant fiber density of 1300 mg/cm$^3$.

The cross sectional area of the fiber is then calculated from the volume, assuming a uniform cylindrical shape for the fiber, as follows:

$$\text{Diameter} = 2 \left( \frac{\text{Vol}}{\pi h} \right)^{\frac{1}{2}}$$

$$\text{Area} = 0.25 \, \pi d^2$$

For simplification, a value of 7566.5, derived from the proceeding equations, times the fiber weight (mgs) gives the cross sectional area in microns squared ($\mu^2$). The force at the breaking point of the fiber in grams divided by the cross sectional area then gives the break strength expressed as gms/$\mu^2$.

$$\text{Break strength} = \frac{\text{Force gms.}}{\text{Area } (\mu^2)}$$

TABLE B

LOSS OF TENSILE STRENGTH WITH REPEATED TREATMENTS

| Composition | Number of Treatments | | | |
| --- | --- | --- | --- | --- |
|  | None | One | Three | Six |
| Waving Lotion[2] | .0287[1] | .0285 | .0233 | .0198 |
| Formula Ex. I | .0287 | .0274 | .0275 | .0249 |

[1] Break strengths in grams per square micron of cross-sectional area
[2] Commercial waving lotion containing ammonium thioglycollate as active ingredient.

TABLE C

COMPOSITION OF DATA OF TABLE B ON BASIS OF PERCENT LOSS[1] OF TENSILE STRENGTH

| Composition | Number of Treatments | | |
| --- | --- | --- | --- |
|  | One | Three | Six |
| Waving Lotion | 0.697 | 18.815 | 31.01 |
| Formula Ex. I | 4.530 | 4.180 | 13.24 |

[1] % loss = 100 − ( (break strength treated / break strength untreated) × 100 )

We claim:

1. Liquid shampoo composition for increasing hair body by permanently swelling hair shafts with reduced loss of tensile strength, consisting essentially of an aqueous solution of a hair cleaning synthetic detergent, which is compatible with the other ingredients, in an effective hair washing concentration for undiluted application which contains on a parts by weight basis from 4 to 10% of bisulfite salt selected from the class consisting of sodium, potassium, ammonium bisulfite, and mixtures thereof, and from 2 to 12% of N.N'-dimethyl urea, said detergent being compatible with said bisulfite and said dimethyl urea, and said composition having a pH from 4.0 to 6.9.

2. The liquid composition of claim 1 in which said bisulfite is sodium bisulfite and is present in an amount of 6.5 to 8.5% by weight.

3. The liquid composition of claim 1 or claim 2 in which said dimethyl urea is present in an amount of 3 to 8% by weight.

4. The liquid composition of claim 1 which also contains from 3 to 10% by weight of water-miscible hydroxalkyl solvent containing from 1 to 3 hydroxyl groups and from 2 to 6 carbons.

5. The liquid composition of claim 1 which also contains from 0.5 to 3% by weight of cationic hair conditioner, said synthetic detergent being compatible with said hair conditioner.

6. The liquid composition of claim 5 in which said synthetic detergent is an amphoteric detergent selected from the class consisting of cocoamidopropyl betaine and cocobetaine.

7. The liquid composition of claim 1 in which said composition has a pH from 6.0 to 6.6.

8. Liquid shampoo composition for increasing hair body by permanently swelling hair shafts with reduced loss of tensile strength, consisting essentially of an aqueous solution of a hair cleansing amphoteric synthetic detergent in an effective hair washing concentration for undiluted application which contains on a parts by weight basis from 4 to 10% of bisulfite salt selected from the class consisting of sodium, potassium, ammonium bisulfite, and mixtures thereof, and from 2 to 12% of N.N'-dimethyl urea, said composition also containing from 2 to 25% of water-miscible hydroxyalkyl containing from 1 to 3 hydroxyl groups and from 2 to 6 carbons, and from 0.5 to 3% of cationic hair conditioner, said composition having a pH from 6.0 to 6.6.

9. The liquid composition of claim 8 in which said bisulfite is sodium bisulfite and is present in an amount of 6.5 to 8.5% by weight.

10. The liquid composition of claim 8 in which said dimethyl urea is present in an amount of 3 to 8% by weight.

11. The liquid composition of claim 8 in which said hydroxyalkyl is propylene glycol and is present in an amount of from 3 to 10% by weight.

12. The liquid composition of claim 8 in which said synthetic detergent is cocoamidopropyl betaine.

13. Liquid shampoo composition for increasing hair body by permanently swelling hair shafts with reduced loss of tensile strength, consisting essentially of an aqueous solution of a hair cleansing amphoteric synthetic detergent in an effective hair washing concentration for undiluted application which contains on a parts by weight basis from 6.5 to 8.5% of bisulfite salt selected from the class consisting of sodium, potassium, ammonium bisulfite, and mixtures thereof, and from 3 to 8% of N.N'-dimethyl urea, said composition also containing from 3 to 10% of water-miscible hydroxyalkyl containing from 1 to 3 hydroxyl groups and from 2 to 6 carbons, and from 0.5 to 3% of cationic hair conditioner, said composition having a pH from 6.0 to 6.6.

14. The liquid composition of claim 13 in which said synthetic detergent is cocoamidopropyl betaine, said bisulfite salt is sodium bisulfite, and said hydroxyalkyl is propylene glycol.

15. The method of using the composition of claim 1 in which said composition is applied to the hair, left thereon for from 3 to 20 minutes, and then rinsed out of the hair with water.

16. The method of using the composition of claim 8 in which said composition is applied to the hair, left thereon for from 3 to 20 minutes, and then rinsed out of the hair with water.

17. The method of using the composition of claim 14 in which said composition is applied to the hair, left thereon for from 3 to 20 minutes, and then rinsed out of the hair with water.

18. The method of claim 15 in which said method is repeated with the same hair a plurality of times with intervening intervals of from 5 to 20 days.

19. The method of claim 16 in which said method is repeated with the same hair a plurality of times with intervening intervals of from 5 to 20 days.

20. The method of claim 17 in which said method is repeated with the same hair a plurality of times with intervening intervals of from 5 to 20 days.

* * * * *